United States Patent [19]

Brill

[11] 4,122,106

[45] Oct. 24, 1978

[54] PROCESS FOR PREPARING THALLIC BENZOATE

[75] Inventor: William F. Brill, Skillman, N.J.

[73] Assignee: Halcon International, Inc., New York, N.Y.

[21] Appl. No.: 804,028

[22] Filed: Jun. 6, 1977

Related U.S. Application Data

[62] Division of Ser. No. 740,150, Nov. 8, 1976, abandoned, which is a division of Ser. No. 679,584, Apr. 23, 1976, Pat. No. 4,021,453.

[51] Int. Cl.$^2$ .............................................. C07F 5/00
[52] U.S. Cl. .............................................. 260/429 R
[58] Field of Search .................................. 260/429 R

[56] References Cited

U.S. PATENT DOCUMENTS

| 3,399,956 | 9/1968 | Hirose et al. | 423/295 |
|---|---|---|---|
| 3,723,517 | 3/1973 | Massie | 260/524 R |

OTHER PUBLICATIONS

Chemical Abstracts, 70, 57071y, (1969).
Chemical Abstracts, 77, 100311k, (1972).
J.A.C.S. 90, (25), pp. 7071–7072, (1968).

*Primary Examiner*—Helen M. S. Sneed
*Attorney, Agent, or Firm*—William C. Long; David Dick; Riggs T. Stewart

[57] ABSTRACT

Olefins are oxidized to produce the corresponding epoxides by means of an aryl thallic carboxylate in the presence of an inert polar organic solvent and in the presence of water, the novel compound thallic benzoate being a preferred reactant.

2 Claims, 1 Drawing Figure

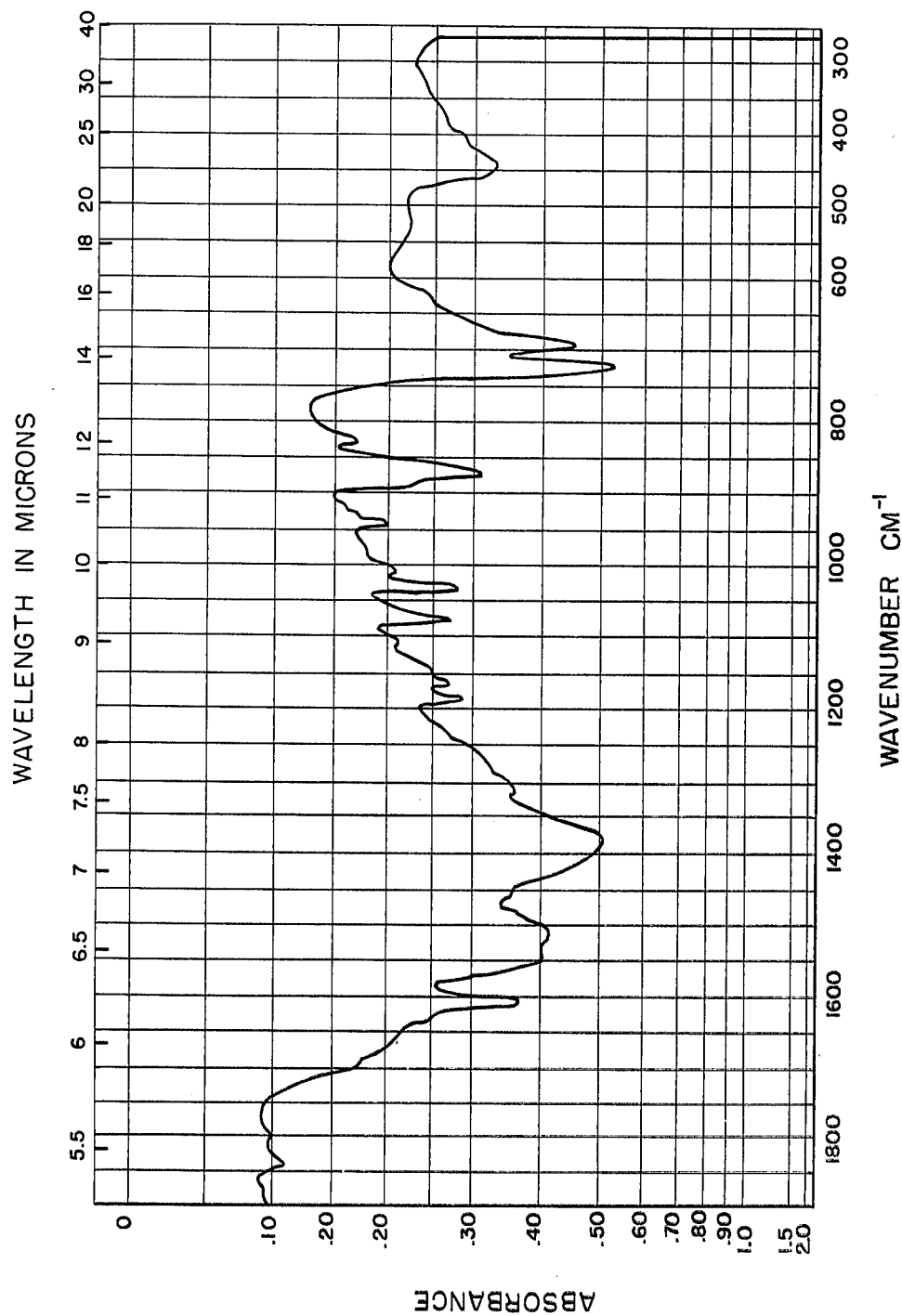

PROCESS FOR PREPARING THALLIC BENZOATE

This is a division, of application Ser. No. 740,150 filed Nov. 8, 1976, now abandoned, which is a division of application Ser. No. 679,584 filed Apr. 23, 1976, now U.S. Pat. No. 4,021,453.

This application relates to the oxidation of olefins and is more particularly concerned with the preparation of epoxides by using thallic salts.

The preparation of certain selected epoxides by the oxidation of the corresponding olefin with thallic acetate is described by Kruse et al, J. Org. Chem. 36 1154 (1971). In this reaction, epoxides of isobutylene and propylene were obtained but only traces of epoxides were detected when ethylene and cis- and trans-2-butene were treated. Even in the case of the epoxidation of isobutylene and propylene, the yields were only moderate.

It is accordingly an object of this invention to provide an improved process for the preparation of epoxides by the oxidation of olefins in the presence of thallic salts.

It is another object of the invention to provide a process of the character indicated which makes possible increased yields of epoxides of isobutylene and propylene.

It is another object of the invention to provide such a process which is effective to produce epoxides from ethylene and other olefins with attractive yields.

Other objects of the invention will be apparent from the following detailed discussion of illustrative embodiments thereof.

In accordance with the invention, olefins are oxidized to produce the corresponding epoxides by means of an aryl thallic carboxylate in the presence of an inert polar organic solvent and in the presence of water. Thus, it has been discovered that epoxides such as ethylene oxide which could not be produced in more than trace quantities by the process of the above-mentioned prior art can be readily produced in good yield when the reaction system contains an aryl thallic carboxylate such as thallic benzoate. At the same time, it has been discovered that aryl thallic carboxylates also effectively epoxidize other olefins to provide greater yields of epoxides of such olefins than have heretofore been obtained by the use of the process of the J. Org. Chem. publication.

The term "olefins" is used herein to include substituted and unsubstituted aliphatic and alicyclic olefinically-unsaturated compounds which may be hydrocarbons or esters or alcohols or ketones or ethers or the like. Preferred compounds are those having from 2–30 carbon atoms. Illustrative olefins are ethylene, propylene, normal butylene, isobutylene, the pentenes, the methyl pentenes, the normal hexenes, the octenes, the dodecenes, cyclohexene, methyl cyclohexene, butadiene, styrene, vinyl toluene, vinyl cyclohexene, the phenyl cyclohexenes, and like hydrocarbon olefins. Olefins having halogen, oxygen, sulfur and like substituents can be used. Such substituted olefins are illustrated by allyl alcohol, methallyl alcohol, diallyl ether, methyl methacrylate, methyl oleate, methyl vinyl ketone, allyl chloride, and the like. In general, all olefinic materials epoxidized by methods previously employed can be epoxidized in accordance with this process. The lower olefins having 2 or 4 carbon atoms in an aliphatic chain are advantageously and readily epoxidized by this process and the class of olefins commonly termed alpha olefins or primary olefins are epoxidized in a particularly efficient manner. It has been discovered that the activity of the process of this invention for the epoxidation of the primary olefins is surprisingly high and can lead to high selectivity to olefin oxides.

The aryl thallic carboxylates which are suitably used in accordance with this invention include the thallium salts of aryl mono-and di-carboxylic acids containing up to 12 carbon atoms in the aryl moiety which may be unsubstituted or substituted with non-reactive substituents such as halogen, amino, alkoxy, alkyl, and the like. Thus, examples of such aryl carboxylic acids include benzoic acid, toluic acid, i.e., o-, m-, and p-toluic acid, nitrobenzoic acid, phthalic acid, chlorobenzoic acid, dichlorobenzoic acid, ethoxybenzoic acid, ethyl benzoic acid, anisic acid, naphthoic acid, anthracene carboxylic acid, and the like.

The thallic aryl carboxylate can be used as the sole thallic carboxylate or it can be used in conjunction with a thallic alkanoate, e.g., containing up to 12 carbon atoms, such as thallic formate, thallic acetate, thallic propionate, thallic butyrate, and the like, preferably thallic acetate. The thallic aryl carboxylate can be preformed or it can be formed in situ, for example by adding the corresponding acid to thallic acetate in any convenient solvent, e.g., the solvent to be used in the epoxidation reaction. When, for example, benzoic acid is added to thallic acetate in solution, e.g., in tetrahydrofuran, at least some of the thallic acetate is converted to thallic benzoate to provide mixed thallic carboxylates. On the other hand, the thallic aryl carboxylate, can, as mentioned, be preformed and used as the only carboxylate in the epoxidation reaction, or the preformed aryl carboxylate can be added to another preformed thallic carboxylate to form mixed thallic carboxylates.

The thallic aryl carboxylate can be preformed by reacting the aromatic acid, e.g., benzoic acid, with thallic oxide in a refluxing non-reactive solvent such as an aromatic solvent, e.g., benzene, and the crystals which form can be used as such or can be further purified by extraction of unreacted acid which may be present with a selective solvent such as ethyl ether, followed by recrystallization from a suitable solvent such as an alcohol, e.g., ethano. Better yields of pure material are, however, obtained by reacting the aromatic acid, e.g., benzoic acid, with thallic nitrate, suitably in an inert solvent, preferably an alcohol such as methyl alcohol. Preferably, the thallic nitrate and the aromatic acid are each dissolved in methyl alcohol and the acid solution is gradually added to the thallic nitrate solution with stirring. The combined solutions are then thoroughly mixed for a few minutes and then allowed to stand. Water is then slowly added with stirring until crystals start to form. Stirring is stopped and the solution is allowed to stand to allow crystals to grow. When no more crystals come out of the solution, the crystals are separated by vacuum filtration. A second crop of crystals can be obtained by adding a further quantity of water, mixing, and then allowing to stand until no further crystals form. The crystals thus recovered are readily dried in a vacuum desiccator.

The preformation of the aryl thallic carboxylate, e.g., thallic benzoate, is preferred since, when benzoic acid is added to aliphatic thallic carboxylates such as thallic acetate, the formation of the desired thallic benzoate is limited. However, even when a preformed aryl thallic carboxylate is used, it is desirable to add with it some free aromatic acid, e.g., benzoic acid, advantageously in the amount of 100 to 500% based upon the aryl thallic carboxylate.

When mixed aryl-nonaryl thallic carboxylates are used, the ratio of the aryl carboxylate to the non-aryl carboxylate is suitably at least 1:1 and preferably is in the range of 5:1 to 10:1.

At least a mole of olefin is generally used per mole of thallic aryl carboxylate but preferably an excess of olefin is employed, and ratios of 2 to 10 moles of olefin per mole of thallic benzoate are most advantageously used. Lower amounts of olefin are, however, operative, e.g., as little as 0.1 mol of olefin per mole of thallic aryl carboxylate.

The epoxidation is carried out, as previously mentioned, in the presence of an inert polar organic solvent, e.g., one having a normal boiling point of at least 75° C., and in the presence of water. Such organic solvents include ethers, alcohols, sulfoxides, amides, nitriles, and the like, such as tetrahydrofuran, dioxane, dimethylformamide, tert-butanol, acetonitrile, dimethylsulfoxide, and the like. Preferred inert polar organic solvents are the cyclic ethers such as tetrahydrofuran and dioxane and the alkanols such as tert-butanol. The amount of water will generally fall between 0.1 and 20 volume % of the water-organic solvent mixture but it preferably is at least 3% and a particularly advantageous quantity is 5-10%. The amount of solvent is freely variable. Most suitably, however, enough is used to dissolve the thallic carboxylate and any free carboxylic acid that may be present and to provide a molar ratio of water to thallic carboxylate of at least 1:1, preferably at least 2:1.

The reaction can be carried out at room temperature, but for best results, from the standpoint of reaction rate, it is advantageous to heat the reaction mixture moderately, e.g., to temperatures of 40° to 100° C., preferably 50° to 60° C.

The reaction is suitably carried out in any vessel into which the solvent-water mixture and the aryl thallic carboxylate can be charged, or formed in situ, and to which the olefin, if normally a liquid, is also charged. In the case of normally gaseous olefins, the reaction vessel is provided with a suitable inlet tube for leading the olefin from its source into the liquid body in the reactor. The reaction can be carried out batch-wise or it can be run continuously. Pressure is not a parameter of the process but the pressure should be sufficient to maintain the solvent in the liquid phase and to keep the olefin in the system. Thus, while the process may be carried out at atmospheric pressure, it is ordinarily desirable to operate at moderate superatmospheric pressure. Ordinarily, pressures greater than 150 psig are not necessary.

The product epoxide is readily recovered from the reaction mixture by distillation, e.g., fractional distillation, and the thallium salts are similarly recovered from the solvent. In the course of the reaction at least some of the thallic ion is reduced to the thallous state. If desired, the thallous ion can be reoxidized to the thallic state in any convenient manner to permit the formation of further quantities of aryl thallic carboxylate. For example, the thallous salt can be air oxidized to produce thallic oxide which can be dissolved in nitric acid to form thallic nitrate and the so produced thallic nitrate can be reacted with an aryl carboxylic acid, e.g., benzoic acid to produce the aryl thallic carboxylate as described above.

The invention will be more fully understood by reference to the following specific examples, but it is to be understood that these examples are given solely for illustrative purposes and are not intended to be limitative of the invention. In the examples the degree of reduction of thallic ion was determined by the iodometric titration. The determination of the epoxide was effected by gas chromatography using a Porapak Q, Carbowax or Silar column depending on the products.

EXAMPLE 1

A 0.1M solution of thallic acetate in a mixture of 90% by volume tetrahydrofuran and 10% by volume water is added to benzoic acid contained in a glass reaction tube to give a clear golden brown solution, the benzoic acid and the thallic acetate being in the molar ratio of 1:0.1. The tube was fitted with a stopper containing a capillary tube extending halfway down its length. The tube was then placed in a pressure vessel and, after evacuating the air present, the vessel was pressured to 100 psi, with ethylene. After rotating the reaction vessel in an oil bath at 60° C. for 30 minutes, it was cooled, the pressure was released and the still clear liquid removed from the tube. Analysis of the oxidate by gas chromatography using a Porapak Q column showed it to contain ethylene oxide in an amount corresponding to a yield of 89% based on thallic carboxylate reacted. Iodometric titration showed that approximately 36% of the thallic ion ($+3$) had been reduced to the thallous ($+1$) state. Selectivity to acetaldehyde was only 9%.

EXAMPLE 2

Following the procedure and using the apparatus described in Example 1, ethylene was replaced by propylene. At the end of the 30-minute reaction period, the oxidate was analyzed and it was found that propylene oxide had been produced in an amount corresponding to a yield of 60% based on the thallic carboxylate reacted as shown by iodometric titration which indicated that approximately 70% of the thallic ion had been reduced to the thallous state. Selectivity to acetone was 19%.

EXAMPLE 3

Example 2 was repeated, except that the molar ratio of benzoic acid to thallic acetate was 0.5 to 0.1. Analysis showed that approximately 40% of the thallic ion had been reduced to the thallous state and that the yield of propylene oxide based on thallic carboxylate reacted was 42%, with the selectivity to acetone 17%.

EXAMPLE 4

Example 2 was again repeated, except that the molar ratio of benzoic acid to thallic acetate was 0.75 to 0.25 and the solvent was composed of a mixture of 70% by volume tetrahydrofuran, 20% by volume water and 10% by volume acetic acid. Analysis showed that about 80% of the thallic ion had been reduced and that the yield of propylene oxide based on carboxylate reacted was 35%, the selectivity to acetone being 29%.

EXAMPLE 5

Example 3 was repeated, except that the benzoic acid was replaced by an equal molar quantity of acetic acid. Analysis of the oxidant showed that 54% of the thallic ion had been reduced to the thallous state and that propylene oxide had been produced in an amount corresponding to a yield of 28% based on thallic carboxylate reacted, with selectivity to acetone being 17%.

EXAMPLE 6

Example 1 was repeated, except that the benzoic acid was replaced by an equal molar quantity of acetic acid. It was found that only 11% of the thallic ion had been reduced to the thallous state and that the yield of ethylene oxide based upon thallic carboxylate reacted was only 7.2%, the selectivity to acetaldehyde being 0.1%.

EXAMPLE 7

A 0.1M solution of thallic acetate in a mixture of 90% by volume tetrahydrofuran and 10% by volume of water is mixed with 4-nitrobenzoic acid in the molar ratio of 4-nitrobenzoic acid to thallic acetate of 1:0.1 in the manner described in Example 1. The reaction vessel was pressured to 100 psi. with ethylene and after reaction for 30 minutes at 60° C. the reaction mixture was cooled and analyzed as described in Example 1. It was found that approximately 30% of the thallic ion had been reduced and that the yield of ethylene oxide was 37% based upon thallic carboxylate reacted, with the selectivity to acetaldehyde being 7%.

EXAMPLE 8

Example 7 was repeated, except that an equal molar quantity of o-toluic acid was substituted for the 4-nitrobenzoic acid. Analysis showed that 23% of the thallic ion had been reduced and that the yield of ethylene oxide was 82% based on thallic carboxylate reacted, with the selectivity to acetaldehyde being 11%.

EXAMPLE 9

Example 7 was again repeated, except that an equal molar quantity of benzene sulfonic acid was substituted for the 4-nitrobenzoic acid. It was found that 96% of the thallic ion had been reduced to the thallous state but only a trace of ethylene oxide had been formed, and the selectivity to acetaldehyde was 18.8%.

EXAMPLE 10

Example 7 was again repeated but the 4-nitrobenzoic acid was replaced by an equal molar quantity of thioacetic acid. Analysis showed that none of the thallic ion had been reduced and that no ethylene oxide had been produced.

EXAMPLE 11

Again repeating Example 7, but replacing the 4-nitrobenzoic acid with an equal molar quantity of p-toluic acid produced an oxidate in which 29% of the thallic ion had been reduced and ethylene oxide had been produced in a quantity corresponding to a yield of 81% based on thallic carboxylate reacted, the selectivity to acetaldehyde being 14%.

EXAMPLE 12

When Example 7 was again repeated, but a equal molar quantity of phthalic acid was substituted for the 4-nitrobenzoic acid, 58% of the thallic ion was reduced to the thallous state and ethylene oxide was produced in a yield of 11.5% based on thallic carboxylate reacted, with a selectivity to acetaldehyde of 15%.

EXAMPLE 13

Using the procedure described in Examples 1 and 7, a 0.1M solution of thallic acetate in a mixture of 90% by volume tetrahydrofuran and 10% by volume of water was mixed with benzoic acid in the molar ratio of benzoic acid to thallic acetate of 1 to 0.1. The reaction vessel was pressured to 100 psi. with cis-butene-2 and the reaction was carried out for 30 minutes at 60° C. The yield of oxide was 11.9%, based on thallic carboxylate charged into the reaction, 10.2% being in the form of cis-butene-2 oxide and 1.7% being in the form of trans-butene-2 oxide.

EXAMPLE 14

When Example 13 was repeated, but with an equal molar quantity of acetic acid being substituted for the benzoic acid, there was no oxide produced.

EXAMPLE 15

Example 13 was again repeated, but the reaction time was extended to 60 minutes. The yield of oxide was 15.6% based upon thallic carboxylate charged, 12% being cis-butene-2 oxide and 3.6% being trans-butene-2 oxide.

EXAMPLE 16

Examples 13, 14, and 15 were repeated, except that trans-butene-2 was substituted for cis-butene-2. When acetic acid was used as in Example 14, no oxide was produced. When, however, benzoic acid was employed as in Examples 13 and 15, 19.8% of oxide was formed after 30 minutes reaction (14.2% trans-butene-2 oxide and 5.6% cis-butene-2 oxide) and 24.4% of the oxide was produced after 60 minutes reaction time (18.5% trans-butene-2 oxide and 5.9% cis-butene-2oxide).

In the foregoing examples the thallic carboxylate of the invention was formed in situ by the addition of an aryl carboxylic acid to thallic acetate. Thallic carboxylate can, however, be preformed in accordance with this invention and the following example shows the preparation of a pure thallic benzoate.

EXAMPLE 17

Thallic nitrate (85.44g) was dissolved in 200 ml. methyl alcohol and 70.44 g. of benzoic acid was dissolved in a second 200 ml. quantity of methyl alcohol. The benzoic acid solution was then slowly added to the thallic nitrate solution with stirring. The solution became cloudy and dark brown in color. After about 15-20 minutes of stirring the solution became clear and had a pale yellow color. The solution was then allowed to stand for 10-15 minutes and 400 ml. of water was added with stirring and the stirring was continued until crystals began to form. The solution turned cloudy when water was added but cleared on standing. When the crystals started to form, the stirring was stopped and the solution was allowed to stand until no more crystals formed (about 3 hours). The crystals were then separated by vacuum filtration and 40 ml. of water was added to the filtrate with stirring until crystals again began to form, which occurred almost immediately upon addition of water. This second crop of crystals was then allowed to grow while the solution was set aside to stand and the crystals were removed by vacuum filtration. The first crop of crystals amounted to 31.2 g. and the second crop was 57.8 g (82% of total yield). Both crops were placed in a vacuum desiccator containing Drierite. The crystals have a melting point of 198° C.±2°. They are slightly soluble in benzene and methanol, readily soluble in acetone, methylethyl ketone and tetrahydrofuran and are insoluble in water and carbon tetrachloride. The infrared spectrum of thallic benzoate is shown in the accompanying drawing.

EXAMPLE 18

Hexene-1 was heated at 60° C. in 1M solution in 90% THF-10% water with 0.2M thallic benzoate as prepared in Example 17 and 0.5M free benzoic acid, yielding 40.5% 1,2-epoxide and 5.7% 2-hexanone in 30 min. and 48% epoxide and 7% ketone in 60 min., based on benzoate charged. No significant byproducts were detected.

EXAMPLE 19

Using thallic benzoate, as prepared in Example 17, cyclohexene was reacted with the thallic benzoate in the presence of free benzoic acid (molar ratio cyclohexene to benzoate to benzoic acid of 1:0.2:1), the benzoic acid being present as a 1M solution in 90% dioxane and 10% water. The reaction was carried out for 30 minutes at 20° C., followed by 30 minutes at 60° C. Analysis of the oxidate showed that 48% of the thallic ion had been reduced and the yield of oxidation products was 90% based upon thallic carboxylate reacted. The oxidation product consisted of 31% cyclohexene oxide and 69% cyclopentene carboxaldehyde, the latter resulting from rearrangement of the carbon skeleton.

EXAMPLE 20

Example 19 was repeated, except that no free benzoic acid was added to the reaction mixture. Analysis showed that 32% of the thallic ion was reduced and the yield of products was 40%. In this case, the cyclohexene oxide represented about 35% of the combined oxide and aldehyde produced.

EXAMPLE 21

Example 19 was again repeated, except that water was omitted and the solvent was entirely dioxane. Very little reaction occurred.

EXAMPLE 22

In another series of experiments involving the preparation of ethylene oxide and using the procedure described in Example 1 with ethylene at 200 psi. and reaction at 60° C. for 30 minutes, operation was carried out using tetrahydrofuran in the presence and in the absence of water and with added benzoic acid or acetic acid (molar ratio of added acid to thallic benzoate, approximately 1:1). In the case of added benzoic acid and a solvent mixture of 90% tetrahydrofuran and 10% water, the yield of ethylene oxide was 25%, but when water was omitted the yield of ethylene oxide was only 0.4%. When acetic acid was added instead of benzoic acid in the system containing 90% tetrahydrofuran and 10% water, the yield of ethylene oxide was 15%, but when the water was omitted only a trace of ethylene oxide was produced. Yields are based on thallic carboxylate charged.

It will be obvious that various changes and modifications may be made without departing from the invention and it is intended, therefore, that all matter contained in the foregoing description and in the drawing shall be interpreted as illustrative only and not as limitative of the invention.

What is claimed is:

1. A process for the preparation of thallic benzoate, which comprises reacting benzoic acid with thallic nitrate in an alcoholic solution.

2. A process as defined in claim 1 wherein the thallic nitrate and the benzoic acid are each dissolved in an alcohol and the two solutions thereafter mixed.

* * * * *